United States Patent [19]

Klein

[11] Patent Number: 5,760,010
[45] Date of Patent: Jun. 2, 1998

[54] METHOD OF TREATING LIVER DISORDERS WITH A MACROLIDE ANTIBIOTIC

[76] Inventor: Ira Klein, 5 Windermere, Houston, Tex. 77063

[21] Appl. No.: 658,837

[22] Filed: May 7, 1996

Related U.S. Application Data

[60] Provisional application No. 60/000,531, Jun. 28, 1995.

[51] Int. Cl.$^6$ .................................................. A61K 31/70
[52] U.S. Cl. .................................................. 514/29; 536/7.2
[58] Field of Search ........................ 514/29; 536/7.2

[56] References Cited

U.S. PATENT DOCUMENTS 4,482,540  11/1984  Gordon et al. .......................... 424/116

OTHER PUBLICATIONS

Physician's Desk Reference®, pp. 421–423, 425–427, 449, 651, 935, 937, 1841, 2102, and 2419 (1995).
Peter B. Gregory, M.D.; "Cirrhosis of the Liver"; Mar. 1995; Scientific American, Inc.
Achord, J.L., *Review of Alcoholic Hepatitis, and Its Treatment*, The American Journal of Gastroenterology, 88(11):1822–1828 (1993).
Alpers, D.H., et al., *Fatty Liver: Biochemical and Clinical Aspects*, Diseases of the Liver, 4th Ed., Chap. 25, pp. 815–829, 1224–1228 (1975).
Bacon, B.R., et al., *Nonalcoholic Steatohepatitis: An Expanded Clinical Entity*, Gastroenterology, 107:1103–1109 (1994).
Cohen, et al., *The SGOT/SGPT Ratio: An Indicator of Alcoholic Liver Disease*, Dig. Dis. Sci., 24:835–838 (1979).
Goldberg, et al., *VA Cooperative Study on Alcoholic Hepatitis IV*, American Journal of Gastroenterology, 81:1029–1034 (1986).
Gregory, P.G., *Cirrhosis of the Liver* in Scientific American Medicine for Gastroenterology, pp. 1–18 (1995).
Isselbacher, K.J., et al., *Infiltrative and Metabolic Disease Affecting the Liver* in Harrison's Principles of Internal Medicine eds. Brawnald, E. et al., pp. 1353–1354 (1988).

Ludwig, et al., *Nonalcoholic Steatohepatitis. Mayo Clinic Experiences With A Hitherto Unnamed Disease*, Mayo Clinical Proceedings, 55:434–438 (1980).
*Metropolitan Height and Weight Tables*, Metropolitan Life Insurance Company, New York (1983).
Physicians' Desk Reference®, pp. 405–408, 1789–1791 (1994).
Physicians' Desk Reference®, pp. 421–423, 425–427, 449, 651, 935, 937, 1841, and 2102 (1995).
Reye, et al., *Encephalopathy and fatty degeneration of the viscera*, Lancet, 2:749 (1963).
Schubert, et al., *Encephalopathy and Fatty Liver (Reye's Syndrome)*, In: Popper, H., et al., (Eds.): Progress in Liver Diseases, 4th Ed., Grune and Stratton, Inc., New York, Chap. 28, pp. 489–510 (1972).

*Primary Examiner*—Elli Peselev
*Attorney, Agent, or Firm*—Fish & Richardson P.C., P.A.

[57] ABSTRACT

This invention is directed to a novel method for treating humans with liver diseases or liver disorders with a macrolide antibiotic. Many different liver disorders can be treated with the claimed invention but this invention is specifically directed to treating nonalcoholic steatohepatitis, alcoholic hepatitis, and Reye's Syndrome. More specifically, this invention is directed to the oral administration of an erythromycin compound or an erythromycin derivative for the treatment of liver disease or liver disorders. The routes of administration can include oral, intramuscular, subcutaneous, transdermal, intravenous or other common routes of administering a drug to a patient. Alternate routes for patients diagnosed with alcoholic hepatitis or Reye's Syndrome are extremely important as oral administration would not be effective due to the patient's clinical symptoms. Most specifically, this invention teaches the novel oral administration of clarithromycin, troleandomycin, erythromycin, or azithromycin for treating human patients with liver disease or liver disorders, including but not limited to nonalcoholic steatohepatitis, alcoholic hepatitis, and Reye's Syndrome.

50 Claims, 7 Drawing Sheets

DATA FROM "PATIENT 5 LIVER DATA"

DATA FROM "PATIENT 5 LIVER DATA"

DATA FROM "PATIENT 6 LIVER DATA"

DATA FROM "PATIENT 6 LIVER DATA"

METHOD OF TREATING LIVER DISORDERS WITH A MACROLIDE ANTIBIOTIC

CROSS REFERENCE TO RELATED APPLICATION

This application is related to the provisional application filed Jun. 28, 1995 having Ser. No. 60/000,531.

TECHNICAL FIELD OF THE INVENTION

This invention is related to U.S. patent application having Ser. No. 08/348,366 which was filed on Nov. 30, 1994, now U.S. Pat. No. 5,498,424, and is entitled "Method of Treating Obesity" (herein incorporated by reference).

This invention relates to methods and compositions for treating human patients with liver diseases or liver disorders with a macrolide antibiotic. Many different liver disorders can be treated by the method of the claimed invention, including nonalcoholic steatohepatitis, alcoholic hepatitis and Reye's Syndrome. More specifically, this invention is directed to the administration (oral or by any other route) of an erythromycin compound or an erythromycin derivative for the treatment of liver diseases or liver disorders. Most specifically, this invention teaches the oral administration of clarithromycin, troleandomycin, erythromycin, or azithromycin for treating human patients with liver disease or liver disorders, including but not limited to nonalcoholic steatohepatitis (fatty liver associated with obesity), alcoholic hepatitis and Reye's Syndrome.

BACKGROUND OF THE INVENTION

Many different liver disorders or liver diseases are associated with liver dysfunction, (e.g., nonalcoholic steatohepatitis, fatty liver associated with obesity, fatty liver hepatitis, alcoholic hepatitis or Reye's Syndrome). These examples will be briefly discussed below.

A. Nonalcoholic Steatohepatitis (Fatty Liver Associated with Obesity)

Nonalcoholic steatohepatitis, also known as nonalcoholic Laennec's, fatty liver hepatitis, fatty liver associated with obesity, steatonecrosis, and diabetic hepatitis, is an increasingly recognized clinical condition (Ludwig et al., *Nonalcoholic Steatohepatitis. Mayo Clinic Experiences With A Hitherto Unnamed Disease*, Mayo Clinic Proceedings, 55:434–438), 1980). Moreover,this condition has been recognized as a progressive disorder which can lead to irreversible liver disease (e.g., fibrosis or cirrhosis) in a relatively short period of time. No specific therapy for this form of cirrhosis is currently available. (Gregory, P. G. *Cirrhosis of the Liver* in Scientific American Medicine for Gastroenterology, pp. 1–18, 1995). For this invention, all of the known (common or uncommon) terms for nonalcoholic steatohepatitis (e.g., "fatty liver of obesity," "fatty liver hepatitis," "nonalcoholic steatohepatitis," etc.) are used interchangeably.

The accumulation of excessive lipid in the liver has been referred to by a variety of terms including fatty infiltration, fatty metamorphosis and fatty degeneration of the liver. By chemical criteria, a fatty liver usually is synonymous with the hepatic accumulation of triglyceride. In the normal liver, triglyceride is not readily evident by light microscopy, but if special lipid stains are used one may see small lipid droplets in the hepatocytes. In a normal liver, approximately 5% of the weight is due to fat. The major hepatic lipids include phospholipids, triglycerides, fatty acids, cholesterol and cholesterol esters. During fat accumulation 40–50% of its liver weight may be due to lipids, mostly in the form of triglyceride. As one of their main toxic effects, many different chemical and pharmacologic agents cause the production of a fatty liver. However, in most clinical situations in which a fatty liver is found, it is usually only one part of a broader metabolic derangement which often includes necrosis. Perhaps the most common occurrence of fatty liver in the United States is associated with alcoholism (see the discussion on alcoholic hepatitis below).

The diagnosis of nonalcoholic steatohepatitis is initially based on findings of hepatomegaly, right upper quadrant abdominal pain, fatigue, malaise, and elevated plasma levels of liver enzymes (e.g., alanine aminotransferase, aspartate aminotransferase, alkaline phosphatase, or γ-glutamyl transpeptidase).

Confirmation of the diagnosis of nonalcoholic steatohepatitis in patients having a negative history of alcoholism and a negative serological workup (e.g., hepatitis B and C serology and autoimmune serology) may be achieved by liver biopsy. Liver biopsy may reveal varying degrees of steatosis, fibrosis, and cirrhosis. In addition, patients with nonalcoholic steatohepatitis may present with abnormal serum (e.g., elevated transferrin saturation or ferritin levels) and abnormal liver iron studies (e.g., elevated hepatic iron concentration and iron staining). (Bacon, B. R. et al, *Nonalcoholic Steatohepatitis: An Expanded Clinical Entity*, Gastroenterology, 107:1103–1109, 1994).

The major causes of fatty liver include: (1) protein malnutrition; (2) diabetes mellitus; (3) obesity; (4) corticosteroid treatment; (5) jejunoileal bypass; (6) chronic illnesses associated with impaired nutrition or malabsorption; (7) intravenous hyperalimentation; and (8) pregnancy. (Isselbacher, K. J. and D. K. Podosky, *Infiltrative and Metabolic Diseased affecting the Liver* in Harrison's Principles of Internal Medicine Eds. Brawnwald, E. et al pp. 1353–54, 1988). Although these causes appear disparate, it has been hypothesized that the accumulation of fat in the liver can be attributed to a perturbation of one of the following steps in the lipid metabolism of hepatocytes and adipocytes: (1) increase free fatty acid delivery to the liver; (2) increased free fatty acid synthesis within the liver; (3) decreased beta-oxidation of fatty acids; and (4) decreased very low-density lipoprotein synthesis or secretion. (Bacon, B. R. et al, *Nonalcoholic Steatohepatitis: An Expanded Clinical Entity*, Gastroenterology, 107:1103–1109, 1994).

Bacon et al recently presented a clinical study of patients with nonalcoholic steatohepatitis (Bacon, B. R. et al, *Nonalcoholic Steatohepatitis: An Expanded Clinical Entity*, Gastroenterology, 107:1103–1109, 1994). In the past, a "typical" patient with nonalcoholic steatohepatitis was a middle-aged, obese women who often had hyperglycemia (with or without diabetes) and/or hyperlipidemia with other medical conditions (e.g. hypertension, hypothyroidism, and coronary artery disease) often requiring use of long-term medications. Bacon et al studied patients with nonalcoholic steatohepatitis who presented a different clinical profile. From their study of the clinical, biochemical, and histological features of 33 patients (mean age 47 years, all patients antibody negative to hepatitis C virus) with nonalcoholic steatohepatitis Bacon et al made the following conclusions. Fifty-eight percent (58%; 19 of 33) were men, 61% of whom were nonobese, 79% had normal glucose levels and 79% had normal lipid levels. Forty-two percent (42%) of the entire group of 33 had normal glucose levels, normal lipid levels, and were not obese. Thirteen of 33 (39%) had pathological increases in fibrosis. Of these 13 with severe, progressive disease, 8 (62%) were women, 8 (62%) were obese, 4 (31%) were diabetic or had an elevated glucose level, and 3 (23%) had hyperlipidemia. Although serum iron studies (transferrin saturation and ferritin) were abnormal in 58% of the patients, no patient had hemochromatosis. Bacon et al concluded that nonalcoholic steatohepatitis can be a severe, progressive liver disease leading to the development of cirrhosis and it should no longer be considered a disease seen predominately in obese women with diabetes.

Depending, in part, on the timing and success of treatment, the clinical outcome of treating patients with nonalcoholic steatohepatitis may range from complete reversal to progression toward irreversible liver disease. Although its etiology is unclear, the progression of nonalcoholic steatohepatitis to severe liver disease is associated with inflammatory cell infiltration, fibrogenesis, and ultimately cirrhosis. The treatment of nonalcoholic steatohepatitis will depend upon the pathology underlying a particular patient's condition, but may include: (1) adequate nutritional intake; (2) removal of offending toxins; and (3) correction of associated metabolic disorders. Weight loss, control of diabetes, and correction of intestinal absorptive defects may also facilitate recovery. This invention provides a useful adjuvant to such treatments by normalizing elevations in plasma levels of liver enzymes and abnormalities in plasma iron studies. In addition to these treatments, the claimed invention is directed to the oral administration of an effective dose of erythromycin or an erythromycin compound to treat patients with nonalcoholic hepatitis.

B. Alcoholic Hepatitis

The clinical profile found in patients with fatty liver tend to be similar, but the best descriptions are those associated with alcohol ingestion, thus the name "alcoholic hepatitis." See Achord, J. L., *Review of Alcoholic Hepatitis and Its Treatment*, The American Journal of Gastroenterology, 88(11):1822–1828, 1993. Alcoholic hepatitis, also referred to as "florid cirrhosis," "toxic hepatitis" and "acute alcoholic hepatitis," is not a syndrome separate from alcoholic fatty liver. Necrosis is merely another manifestation of hepatic injury related to alcohol. Although on a liver biopsy, much fat can be observed, fat may also be almost totally absent. In addition, liver biopsy may be marked by cell necrosis, polymorphonuclear inflammatory infiltrate of variable intensity and fatty metamorphosis. All of the acute changes induced by alcohol (e.g., fatty liver, alcoholic hepatitis and acute fatty liver with cholestasis) are potentially reversible. The diagnosis can be suspected clinically, but differential diagnosis is best made by needle biopsy of the liver.

In a large Veterans Administration study of alcoholic patients, 51% had been admitted for signs unrelated to liver disease (Goldberg, et al, *VA Cooperative Study on Alcoholic Hepatitis IV*, American Journal of Gastroenterology, 81:1029–1034, 1986). In 49% of the patients the serum bilirubin was normal, 19% had normal AST levels, 37% had normal alkaline phosphatase levels and 59% had normal serum albumin levels. Despite this "mild" clinical disease, 38% had cirrhosis and mortality was 22% at 30 months.

The typical patient hospitalized with acute alcoholic hepatitis is anorectic and has been consuming more than 80–160 g of alcohol per day for several weeks, months or years. Most have hyperbilirubinemia, are often febrile and have tender hepatomegaly. The characteristic laboratory findings include leukocytosis, hypoalbuminemia, elevated alkaline phosphatase, elevated AST and normal or only modestly elevated ("ALT"). It is rare for the AST to reach levels of greater than 600 IU in the usual patient. An AST:ALT ratio of >2 is about 68% sensitive and 91% specific for alcoholic liver disease with a positive predictive value of 82% (Cohen et al, *The SGOT/SGPT Ratio: An Indicator of Alcoholic Liver Disease*, Dig. Dis. Sci., 24:835–838 1979; γ-glutamyl transpeptidase=GGT, aspartate aminotransferase=AST or SGOT, alanine aminotransferase=ALT or SGPT).

The acute hepatic lesions associated with alcohol sometimes cannot be clearly separated pathologically from each other. Although the lesions are reversible, the change may occur very slowly while it is not unusual for recovery to begin after only two to three weeks of hospitalization, while total recovery may require months. Treatment normally is supportive and the mainstay of therapy is abstinence from alcohol. This invention adds yet another parameter in treating patients diagnosed with alcoholic hepatitis. In addition to abstinence, the claimed invention is directed to the oral administration of an effective dose of erythromycin or an erythromycin derivative to treat patients with alcoholic hepatitis.

C. Reye's Syndrome

The syndrome of encephalopathy and fatty liver was first defined by Reye in 1963 (see Reye, et al, *Encephalopathy and fatty degeneration of the viscera*, Lancet, 2:749 (1963); Schubert et al, *Encephalopathy and Fatty Liver (Reye's Syndrome)*, in: Popper, H. and Schaffner, F. (eds.): Progress in Liver Diseases. Chap. 28, 4th Edition, New York, Grune and Stratton, Inc., 1972, pp. 489–510). The causes are unknown and may be multiple. Even with today's technological advances, the mortality rate is still very high at 38%.

The clinical picture includes disturbed consciousness following a usually trivial prodromal illness that includes vomiting. Of 30 cases studied during 1963–1972, 11 were boys and 19 were girls, ages ranging from 4 months to 14 years old. All had a prodromal illness from 2 days to 3 weeks before the onset of encephalopathy. The prodromal illness lasted from 5 to 7 days before the onset of the central nervous system signs. All children vomited two days before onset of encephalopathy. Total serum bilirubin levels were below 3 mg percent and the urine did not contain bile. The liver was usually not enlarged at admission, but after 12–24 hours of encephalopathy, the liver was palpable. The neurologic symptoms are graded in severity from mild lethargy to decerebrate posturing and seizures. Four clinical grades of Reye's Syndrome at time of admission have been delineated:

Clinical Grade 1: Usually quiet or mildly lethargic;
Clinical Grade 2: Deep lethargy, confusion, may have brief unconsciousness;
Clinical Grade 3: Extreme lethargy or light coma lasting less than 3 hours; some seizures and/or agitation;
Clinical Grade 4: Seizures, agitated, deep coma lasting longer than 3 hours, intermittent decerebrate posturing;
Clinical Grade 5: Seizures, deep coma, decerebrate posturing and fixed pupils.

Accurate diagnosis demands liver biopsy. Grossly, the liver is yellow orange, pale yellow or occasionally white. Characteristic pathological lesions are acute fatty infiltration of the liver. In children who recover, light microscopy of the liver is normal within 2 months except for remaining fat droplets in lipocytes and Kupffer cells. The changes occur uniformly in all hepatic cells, suggesting injury by a soluble substance or deficiency of some substrate or co-factor.

In view of the above discussion of the enormity of the different liver diseases and liver disorders, an inexpensive, easy to administer, physically tolerable and effective treatment for this group of diseases is clearly needed. The claimed invention solves this problem by teaching the administration of an effective amount of an antibiotic to a human patient diagnosed with liver disease. The liver diseases treated by the claimed invention, include, but are not limited to, nonalcoholic steatohepatitis, alcoholic hepatitis, and Reye's Syndrome. More specifically, the antibiotic used in this invention is erythromycin or an erythromycin derivative, including but not limited to clarithromycin, troleandomycin, erythromycin, or azithromycin. Thus, the claimed invention offers a solution to the serious health problems facing most Americans diagnosed with a liver disease or liver disorder.

SUMMARY OF THE INVENTION

The claimed invention is a novel method of treating liver diseases or disorders with a macrolide antibiotic. Examples of liver diseases or liver disorders include nonalcoholic steatohepatitis, alcoholic hepatitis and Reye's Syndrome. These examples are listed as examples only and the list is not intended to limit the claimed invention to these diseases. The claimed method of treating liver diseases or liver dysfunctions includes administering to a human an effective amount for treating the liver disease of an erythromycin compound. More specifically, the erythromycin compound or erythromycin derivative used in this invention includes, but is not limited to, clarithromycin, troleandomycin, erythromycin, or azithromycin.

One aspect of this invention is a method of treating a human having a liver disorder or liver disease comprising administering to the human an effective dose for treating the liver disorder of an erythromycin compound. In one embodiment of this method, the erythromycin compound is selected from the group consisting of clarithromycin, troleandomycin, erythromycin, and azithromycin. In a preferred embodiment, the dose is administered orally and ranges from 100 mg/day to 6,000 mg/day. This invention is directed to the administration (oral or by any other route) of an erythromycin compound or an erythromycin derivative for the treatment of liver disease or liver disorders. In yet another preferred embodiment of this invention, the routes of administration can include oral, intramuscular, subcutaneous, transdermal, intravenous or other common routes of administering a drug to a patient. Alternate routes for patients diagnosed with alcoholic hepatitis or Reye's Syndrome are extremely important as oral administration would not be effective due to the patient's clinical symptoms. In an alternative embodiment, the dose is administered to the human by any known route and ranges from 1 mg/kg of body weight/day to 100 mg/kg of body weight/day.

An alternative aspect of this invention is a method of reducing the plasma activity of a liver enzyme in a human patient comprising administering to the human an effective dose for reducing the plasma activity of a liver enzyme of an erythromycin compound. In an alternative embodiment of this method, the liver enzyme is selected from the group consisting of aminotransferase and transpeptidase, wherein the aminotransferase is further selected from the group consisting of aspartate aminotransferase and alanine aminotransferase. In an alternative embodiment of this invention, the transpeptidase is further defined as γ-glutamyl transpeptidase. In another embodiment of this method, the erythromycin compound is selected from the group consisting of clarithromycin, troleandomycin, erythromycin, and azithromycin. In a preferred embodiment, the dose is administered orally and ranges from 100 mg/day to 6,000 mg/day.

In an alternative embodiment, the dose is administered to the human by any known route and ranges from 1 mg/kg of body weight/day to 100 mg/kg of body weight/day.

DESCRIPTION OF THE PREFERRED EMBODIMENTS

Figure 1A:
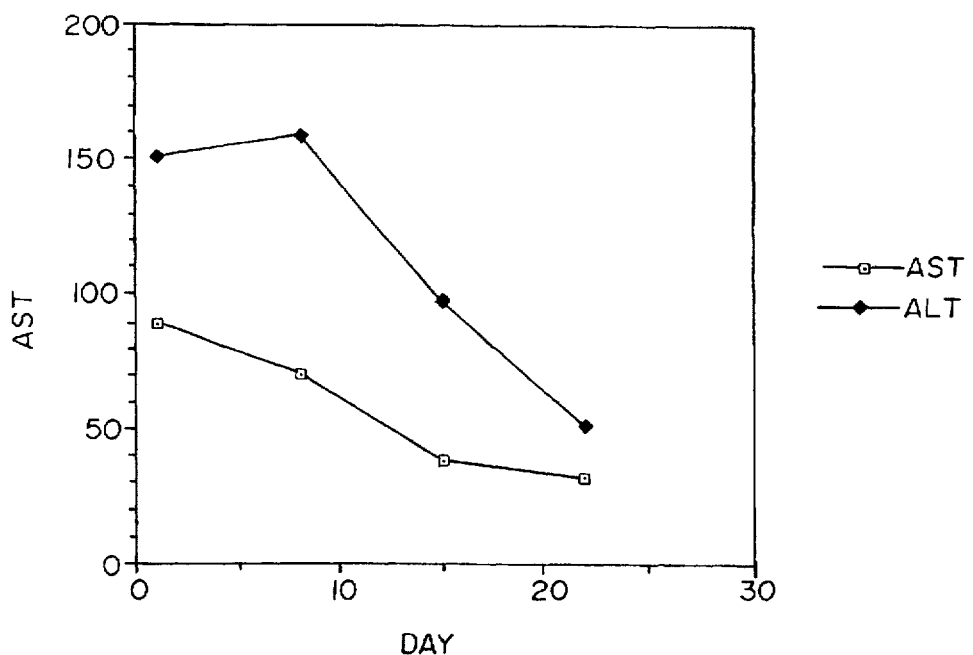
FIG. 1 Panels A, B, and C detail liver enzyme levels for Patient #1.

This invention relates to methods and compositions for treating human patients with liver disease or liver disorders. Many different liver disorders can be treated with the claimed invention but specifically include nonalcoholic steatohepatitis alcoholic hepatitis and Reye's Syndrome. More specifically, this invention is directed to the administration (oral or by any other route) of an erythromycin compound or an erythromycin derivative for the treatment of liver disease or liver disorders. The routes of administration can also include oral, intramuscular, subcutaneous, transdermal, intravenous or other common routes of administering a drug to a patient. Alternate routes for patients diagnosed with alcoholic hepatitis or Reye's Syndrome are extremely important as oral administration would not be effective due to the patient's clinical symptoms. Most specifically, this invention teaches the oral administration of clarithromycin, troleandomycin, erythromycin, or azithromycin for treating human patients with liver diseases or liver disorders, including but not limited to nonalcoholic steatohepatitis, alcoholic hepatitis, and Reye's Syndrome.

As stated above, the routes of administration can also include oral, intramuscular, subcutaneous, transdermal, intravenous or other common routes of administering a drug to a patient. For example, the pharmaceutical compositions of the claimed erythromycin or erythromycin derivatives are formulated so as to be suitable for oral administration. The active ingredient (erythromycin or erythromycin derivative) is contained in a capsule or tablet, preferably in enteric form. The quantity of effective dose supplied by each capsule or tablet is relatively unimportant because the desired total dosage can be reached by administration of either one or a plurality of capsules or tablets or both. The capsules employed may comprise any well known pharmaceutically acceptable material such as gelatin, cellulose derivatives, etc. The tablets may be formulated in accordance with conventional procedures employing solid carriers, lubricants, etc., well known to those skilled in the art. Examples of solid carriers are: starch, sugar, bentonite and other commonly used carriers.

DEFINITIONS

For the purpose of this invention, certain phrases and words are defined or used as follows:
1. "dose" and "amount" (e.g. "effective dose") are interchangeably used;
2. "liver disease," "liver disorder," "liver dysfunction," and "dysfunctional liver" are used interchangeably and include, but are not limited to, nonalcoholic steatohepatitis, alcoholic hepatitis, and Reye's Syndrome.

3. "erythromycin" or an "erythromycin derivative" are used interchangeably and have the following meaning: a macrolide antibiotic which is a lipophilic molecule with a characteristic central lactone ring bearing 12 to 17 atoms, fewer than 5 and preferably no double bonds and preferably no nitrogen bonds. Several amino and/or neutral sugars are preferably fixed to the lactone ring. Examples of preferred erythromycin and erythromycin derivatives include: erythromycin, clarithromycin, azithromycin, and troleandomycin.

4. All of the known terms for nonalcoholic steatohepatitis, e.g. "fatty liver of obesity," "fatty liver hepatitis," "nonalcoholic steatohepatitis," etc. are used interchangeably.

5. γ-glutamyl transpeptidase or gamma glutamyl transferase means GGT, aspartate aminotransferase means AST or SGOT and alanine aminotransferase means ALT or SGPT.

6. Obese is greater than 10% above ideal body weight using Metropolitan Life Insurance Standards (*Metropolitan Height and Weight Tables*. New York: Metropolitan Life Insurance Company, 1983).

7. "treat" means to normalize the clinical profile associated with the specific liver disease or disorder being treated by the administration of erythromycin or an erythromycin derivative.

8. For this patent application, examples of liver diseases or liver disorders include nonalcoholic steatohepatitis, alcoholic hepatitis and Reye's Syndrome. These examples are listed as examples only and the list is not intended to limit the claimed invention to these diseases.

9. Clarithromycin and Biaxin™ are used interchangeably. For example, ten 10 milligrams of Biaxin™ or ten (10) milligrams of clarithromycin per pound of body weight was administered at 48 hour intervals to patients diagnosed with a liver disorder.

10. A clinical definition of a liver disorder or a liver disease is a patient with a plasma AST level of greater than 49 U/L or a plasma ALT level of greater than 54 U/L. An abnormal plasma GGT level (greater than 66 U/L for men, greater than 33 U/L for women) alone or an abnormal plasma ferritin level (outside of the range of 23–233 ng/ml) alone is not specific for a liver disease or liver disorder in and of itself. However, an abnormal GGT level (greater than 66 U/L for men, greater than 33 U/L for women) or an abnormal ferritin level (outside of the range of 23–233 ng/ml for men and outside the range of 10–107 ng/ml for women) may be used as an additional marker in a patient initially diagnosed with a liver disease or liver disorder as a result of presenting a plasma AST level of greater than 49 U/L or a plasma ALT level of greater than 54 U/L. Thus, a clinical diagnosis of a liver disease or liver disorder is made when either an elevated plasma AST level is presented or when an elevated plasma ALT level is presented.

11. Note that all patients received ten (10) milligrams of Biaxin® (clarithromycin) per pound of body weight at 24 hour intervals (for nonobese alcoholics) or at 48 hour intervals (for obese alcoholics) for the days indicated in Tables 2 and 3.

12. 1 mg/kg/day=0.45 mg/lb/day; 100 mg/kg/day=45.0 mg/lb/day; 1.0 kg=2.222 lb; and 10 mg/lb =22.2 mg/kg.

13. "ccs" and "mls" are used interchangeably.

EXAMPLES

The following examples illustrate selected modes for carrying out the claimed invention and are not to be construed as limiting the specification and claims in any way. These examples are provided so as to enable those of ordinary skill in the art to make and use the invention. These examples are not intended to limit the scope of what the inventor regards as the invention. Efforts have been made to ensure accuracy with respect to numbers used to characterize the conditions; however, some experimental errors and deviations may be present.

Example 1

Background Information on Macrolide Antibiotics

Macrolide antibiotics have been described by Bryskier, et al (Bryskier, A., Agouridas, C., and Chantot, J. F., *Structure and Activity in* THE NEW MACROLIDES, AZALIDES, AND STREPTOGRAMINS: PHARMACOLOGY AND CLINICAL APPLICATIONS, 3,3–11 (Neu, H. C., Young, L. S., and Zinner, S. H., eds., 1993)) and Omura (Omura, S., *Macrolide Antibiotics—Chemistry, Biology and Practice* 1984).

Macrolide antibiotics include, for example, those described by Bryskier et al, e.g., a lipophilic molecule with a characteristic central lactone ring bearing 12 to 17 atoms, fewer than 5 and preferably no double bonds, and preferably no nitrogen atoms. Several amino and/or neutral sugars are preferably fixed to the lactone ring. One group of somewhat atypical macrolide antibiotics, are lankacidin derivatives, 17 membered-ring macrocyclic antibiotics which do not have sugars fixed to the aglycone ring. Another group of somewhat atypical macrolide antibiotics, are azalide compounds which contain an endocyclic nitrogen, namely azalide, within the aglycone ring.

Examples of macrolide antibiotics include the following synthetic, semi-synthetic or naturally occurring compounds: methymycin, neomethymycin, YC-17, litorin, erythromycin A to F, oleandomycin, roxithromycin, dirithromycin, flurithromycin, clarithromycin, davercin, azithromycin, josamycin, kitasamycin, spiramycin, midecamycin, rokitamycin, miokamycin, lankacidin, and the derivatives of these compounds. Thus, erythromycin and compounds derived from erythromycin belong to the general class of antibiotics known as "macrolides." Examples of preferred erythromycin and erythromycin-like compounds include: erythromycin, clarithromycin, azithromycin, and troleandomycin.

Endomycin, a polyenic macrolide antibiotic, has been used previously to alter lipid metabolism. U.S. Pat. No. 4,482,540 (Issued to Gordon et al on Nov. 13, 1984; incorporated herein by reference) is directed to the oral administration of endomycin for altering lipid metabolism and reducing blood cholesterol levels. The Gordon invention is directed to a process for treating hypercholesterolemia in a mammal comprising the oral administration of an effective dose of endomycin to said mammal. The claimed invention is different from the Gordon invention in that the claimed invention utilizes an erythromycin compound or an erythromycin derivative for treating hypercholesterolemia. Additionally, one of ordinary skill in this art knows that erythromycin (or an erythromycin derivative) is structurally, and chemically different from endomycin (a polyenic macrolide antibiotic). The general class of polyenic macrolide compounds described in the Gordon invention are the hexaenes. The hexaene group of polyenic macrolides is relatively small in comparison to other groups. Representative of this group are mediocidin, endomycin B (synonymous with Helixin B), cryptocidin and flavacid.

Example 2

Erythromycin and Erythromycin Derivatives

1. Clarithromycin

Although the route of administration and dose will depend upon a variety of factors (e.g., treatment environment, patient compliance and tolerance, therapeutic goals, etc.), the preferred dose of clarithromycin is taken orally ranges between 1 mg/kg of body weight/day and 100 mg/kg of body weight/day (i.e., approximately 100 mg/day to 6,000 mg/day).

Clarithromycin, also known as, 6-0-methylerythromycin, has the chemical formula, $C_{38}H_{69}NO_{13}$, and a molecular weight of 747.96 (see Physicians' Desk Reference®, 405–407, 1994). Clarithromycin is commercially available from Abbott Laboratories under the trademark "BIAXIN™", and is described, with other related erythromycin compounds in Watanabe, et al., U.S. Pat. No. 4,331,803 (which is incorporated herein by reference).

2. Azithromycin

In another aspect of the present invention, the erythromycin compound is azithromycin which is derived from erythromycin. It differs from erythromycin in that a methyl substituted nitrogen atom is incorporated into the lactone ring. Although the route of administration and dose will depend upon a variety of factors (e.g., treatment environment, patient compliance, patient tolerance, therapeutic goals, etc.), the preferred dose of azithromycin is taken orally and ranges between 1 mg/kg per body weight/day and 100 mg/kg of body weight/day (i.e., approximately 100 mg/day to 6,000 mg/day). Azithromycin, as a dihydrate, is a white crystalline powder with the chemical formula $C_{38}H_{72}N_2O_{12}2H_2O$ and a molecular weight of 785.0 (see Physician's Desk Reference®, 1789–91, 1994). Azithromycin is commercially available from Pfizer Laboratories under the trademark "ZITHROMAX™".

3. Troleandomycin

In another aspect of the present invention, the erythromycin compound is troleandomycin. Although the route of administration and dose will vary depending upon a variety of factors (e.g., treatment environment, patient compliance and tolerance, therapeutic goals, etc.), the preferred dose of troleandomycin is taken orally and ranges between 1 mg/kg of body weight/day and 100 mg/kg of body weight/day (i.e., approximately 100 mg/day to 6,000 mg/day). Troleandomycin has the chemical formula $C_{41}H_{67}NO_{15}$, and a molecular weight of 814 (see Physicians' Desk Reference@, 2102, 1995). Troleandomycin is commercially available from Pfizer Roerig Division under the trademark "TAO™".

4. Erthromycin

In another aspect of the present invention, the erythromycin compound is erythromycin (i.e., including, but not limited to, erythromycin ethylsuccinate, erythromycin estolate, erythromycin stearate, and erythromycin lactobionate). Erythromycin is produced by a strain of *Streptomyces erythrueus* and belongs to the macrolide group of antibiotics. It is basic and readily forms salts with acids, but it is the base which is pharmacologically active. Although the route of administration and dose will depend upon a variety of factors (e.g., treatment environment, patient compliance, tolerance, therapeutic goal, etc.), the preferred dose of erythromycin is taken orally and ranges between 1 mg/kg of body weight/day and 100 mg/kg of body weight/day (i e., approximately 100 mg/day to 6,000 mg/day). Erythromycin has the chemical formula -$C_{37}H_{67}NO_{13}$ and a molecular weight of 733.92 (see Physicians' Desk Reference®, 421–423, 425–427, 449, 651, 935, 937, 1841, and 2102, 1995). Erythromycin is commercially available from Abbott Laboratories, Boots Laboratories, Parke-Davis,. Dista, and Ross Laboratories under different trademark names including, but not limited to, "Erythromycin Delayed-released Capsules (USP)™".

Example 3

"Normal" Plasma Concentrations of Liver Enzymes and General Information Given to each Patient Prior to Beginning Biazin Treatment A preferred aspect of the present invention is a method of treating liver disorders or liver diseases which includes administering an effective dose or amount of an erythromycin or erythromycin derived compound to a human patient with a clinical diagnosis of a liver disorder or disease. Patients are diagnosed as having a liver disease or disorder when the plasma concentrations of their liver enzymes are out of the "normal" range. Table 1 below lists the "normal" ranges for the plasma concentrations of liver enzymes that are followed during the course of the patient's treatment for their liver disease or disorder. For this invention, a clinical definition of a liver disorder or a liver disease is a patient with a plasma AST level of greater than 49 U/L or a plasma ALT level of greater than 54 U/L. An abnormal plasma GGT level (greater than 66 U/L for men, greater than 33 U/L for women) alone or an abnormal plasma ferritin level (outside of the range of 23–233 ng/ml for men and outside of the range of 10–107 ng/ml for women) alone is not specific for a liver disease or liver disorder in and of itself. However, an abnormal GGT level or an abnormal ferritin level may be used as an additional marker in a patient initially diagnosed with a liver disease or liver disorder as a result of presenting a plasma AST level of greater than 49 U/L or a plasma ALT level of greater than 54 U/L. Thus, a clinical diagnosis of a liver disease or liver disorder is made when either an elevated plasma AST level is presented or when an elevated plasma ALT level is presented.

TABLE 1

| NORMAL RANGE FOR PLASMA LEVELS OF LIVER ENZYME | |
|---|---|
| PLASMA COMPONENT | "Normal" Plasma Concentration |
| AST | <49 U/L |
| ALT | <54 U/L |
| GGT | <66 U/L (Male) |
|  | <33 U/L (Female) |
| Ferritin | 23–233 ng/ml (Male) |
|  | 10–107 ng/ml (Female) |

NOTE:
γ-glutamyl transpeptidase or gamma glutamyl transferase means GGT, aspartate aminotransferase means AST, alanine aminotransferase means ALT

General Information Given To Each Patient Beginning Biaxin™ Treatment

An informed consent was obtained from all patients with regard to the potential benefits and risks of the experimental protocol. Each patient was informed that clarithromycin has not yet been approved by the F.D.A. for the treatment of liver dysfunction. Many patients who are obese also have a diagnosed liver disorder or liver disease. Many, if not all of liver diseases, are serious illnesses that can progress to cirrhosis of the liver apart from any history of alcohol ingestion or prior viral hepatitis. Thus, a new trial was initiated for the treatment of liver disorders with clarithromycin (e.g., nonalcoholic steatohepatitis, alcoholic hepatitis and Reye's Syndrome) and being overweight was not a factor for inclusion in this study.

All current medications were reviewed in detail for each patient by the physician. Patients on certain medications or with histories of certain diseases were excluded from participation in the trial. A detailed history of alcohol ingestion was obtained for each patient and all patients were emphatically informed that alcohol consumption was prohibited. Wherever possible, a liver biopsy prior to initiation of clarithromycin therapy and at the completion of the treatment was, or will be obtained.

A physical examination is performed on all patients. Hypertension is extremely common in this patient population. Patients on angiotensin conversion enzyme (ACE) inhibitors were transferred to an alpha blocker, prazosin, if they were diabetic, and to a beta blocker, atenolol, if they were not diabetic. Beta blockers should be avoided with diabetes mellitus as they may hide the symptoms of hypoglycemia. Optimum control of diabetes was provided with either insulin, or oral hypoglycemic medication where indicated.

All patients had a CBC and SMA-29 work-up on the days indicated in Tables 2 and 3 (usually weeks 0, 1, 2, 3, 4 and every 4 weeks thereafter or day 1, 8, 15, 22, and 29). For the CBC workup, 5 ml of blood was drawn into a Vacutainer™ with 0.05 ml of 15% EDTA(K3) solution (7.5 mg). There was no interior coating, the tube had a silicone lubricated stopper and a lavender top for identification. For the SMA-29 work-up, 5 ml of blood was drawn into an empty Vacutainer™ with a red top for identification. The blood was centrifuged and the results were obtained by examination of the serum by an automated processor. These automated processors are readily available through routine laboratory services provided to all clinicians. The automated processors are calibrated and routinely checked and re-calibrated.

The inventor observed that women develop nausea more frequently with ingestion of clarithromycin. All women were instructed to take a 250 mg tablet of Tigan™ (Physicians' Desk Reference, page 2419, 1995) upon awakening the day that clarithromycin is to be taken. The women were instructed to wait 30 minutes after taking Tigan™ before taking the full dose of clarithromycin (taken with water only). The clarithromycin is not to be taken with food. Men were instructed to take the clarithromycin on awakening without food.

Patients were informed that they could have a bad taste in their mouth as a result of the medication. Patients were told that additional side effects (abdominal cramps, nausea, diarrhea) may occur during the first and second doses. These symptoms should decrease thereafter with continued use. Some patients have reported one or two loose bowel movements within 4 hours of taking the medication. All patients were advised that the diarrhea should not persist. Patients were advised that if there is any suspicion of an allergic reaction (hives, skin rash, difficulty breathing) they should call a physician immediately. Patients were also advised that any persistent diarrhea, fever or rectal bleeding should be evaluated by their physician immediately.

If the patient is overweight, this patient is advised regarding eating habits and food intake. Regarding dietary instructions, patients were advised to avoid ingestion of bread, potatoes, deserts, and snacks. With most patients, simplicity of instructions is important.

A weekly visit for monitoring weight, blood pressure, and blood tests allows the physician to reinforce the importance of diet to improve one's health. The medication was discontinued if any significant abnormalities on the blood tests were observed. In particular, the physician would monitor for increasing hepatic dysfunction, renal dysfunction, decrease of the white blood cell count or platelet count as these can be side effects of the medication (albeit rare side effects).

During the patient-doctor interaction about dieting, the patient is also provided information regarding the mechanism behind successful weight loss and how to maintain weight loss was explained to each patient. The patients are informed that some individuals, no table to maintain weight loss, may lack the effect in the brain to turn off the desire to ingest further food when it is not needed. Recent studies with regard to the obesity gene demonstrate that a protein (ob) is produced by fat cells which normally attaches to a brain receptor site. The effect of this ob protein binding to its receptor is to create a sensation of satiety and turn off the desire to eat further. Obese individuals produce a defective protein that fails to attach to the receptor site in the brain and they continue to consume more food than would otherwise be warranted. Obesity will raise the serum cholesterol. Food that is high in cholesterol content will increase the serum cholesterol. The effect of obesity and high lipid levels in the blood is to increase the fat content in the liver. This leads to hepatic dysfunction as noted with abnormal liver enzymes on the SMA-29.

Once the liver enzymes return to normal, clarithromycin may be discontinued or the patient may continue to take it as a prophylactic therapy. The resetting of the hypothalamic thermostat appears to persist for some time after cessation of taking of the medication and the duration of maintenance of normal liver enzyme levels without medication will be determined on a case-by-case basis. The plasma levels of hepatic enzymes a re closely monitored closely after cessation of medication to determine if further treatment is indicated.

For nonobese alcoholics or patients with a liver disease who are not obese, the endpoint would be normal liver enzyme s and a liver biopsy that demonstrated substantial improvement with regard to the histologic findings of significant hepatic cell fibrosis, necrosis, cirrhosis, or fatty infiltration of the liver. Excessive fat in the liver appears to be a common pathogenetic mechanism associated with the development of hepatic dysfunction for both nonalcoholic steatohepatitis and alcoholic hepatitis. The dose of clarithromycin for treating alcoholic hepatitis in an individual who is not overweight is in the range of 250 mg to 2 grams taken as a single dose each morning on awakening.

Currently, there is no definitive drug treatment for either nonalcoholic steatohepatitis or alcoholic hepatitis. With alcoholic hepatitis, 6 to 18 months is commonly required for liver enzymes to return to normal, even if the patient ceases ingestion of alcohol. Additional studies will be required to determine if clarithromycin can significantly decrease the progression to cirrhosis, hepatic failure, requirement for liver transplantation and death.

Example 4

General Background Information Regarding Administration of Erythromycin or Erythromycin Derived Compounds for Treating Nonalcoholic Steatohepatitis As stated above, this invention is a novel method of treating liver disorders or liver diseases including but limited to nonalcoholic steatohepatitis (fatty liver of obesity), alcoholic hepatitis, and Reye's Syndrome. A preferred aspect of the present invention is a method of treating liver disorders or liver diseases which includes administering an effective dose or amount of an erythromycin or erythromycin derived compound to a human patient with a clinical diagnosis of a liver disorder or disease. Many different erythromycin compounds or erythromycin derived compounds are known to those skilled in this art but the inventors prefer to use erythromycin, clarithromycin, azithromycin, or troleandomycin.

A patient in need of treatment for nonalcoholic steatohepatitis may be identified by measuring plasma levels of liver enzymes (e.g., GGT, AST, ALT) or by other standard diagnostic techniques (e.g., liver biopsy, patient history of malnutrition or alcoholism, abnormal plasma or liver iron studies, etc.). Informed patient consent is obtained and treatment is initiated. A complete medical history is obtained with emphasis on potential adverse reactions to or contraindications for the use of erythromycin compounds. Blood is drawn from the patient and plasma levels of liver enzymes are determined. The desired reduction of plasma levels of liver enzymes is then determined based upon a comparison of the patient's present plasma enzyme levels with normative values and the physician's professional judgment. An effective dose for treating nonalcoholic steatohepatitis, the interval between doses, and the duration of treatment are then determined. The patient is followed at appropriate intervals during treatment and measurements of plasma levels of liver enzymes, patient histories, and dose modification, if necessary, are performed.

Three patients with diagnosed nonalcoholic steatohepatitis were treated with clarithromycin. Five milliliters of blood were drawn from each patient on the days indicated and plasma levels of AST, ALT, and GGT were determined for each patient. The results of such a treatment regime are shown in Table 2. Note that all patients received 10 milligrams of Biaxin™ (clarithromycin) per pound of body weight at 48 hour intervals for the days indicated in Table 2.

General conclusions after fifteen (15) days of Biaxin treatment for these initial three (3) patients demonstrated that:

1. Plasma AST levels decreased by greater than or equal to 10% in 3 out of 3 patients (100%).
2. Plasma ALT levels decreased by greater than or equal to 10% in 3 out of 3 patients (100%).
3. Plasma GGT levels decreased by greater than or equal to 10% in 2 out of 3 patients (67%).
4. Plasma ferritin levels decreased by greater than or equal to 10% in 3 out of 3 patients (100%).

Example 5

Figure 1B:
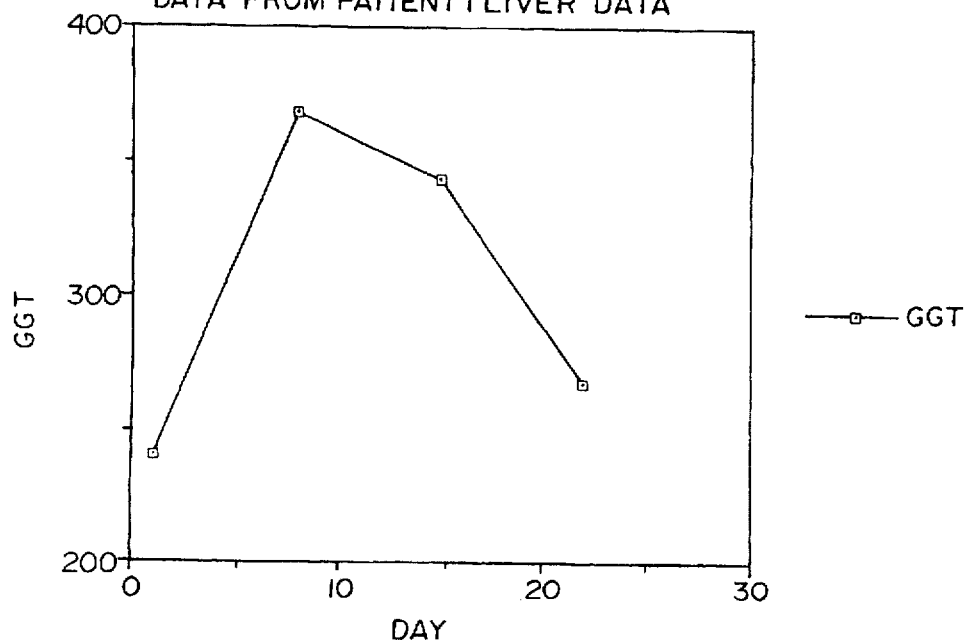
Figure 1C:
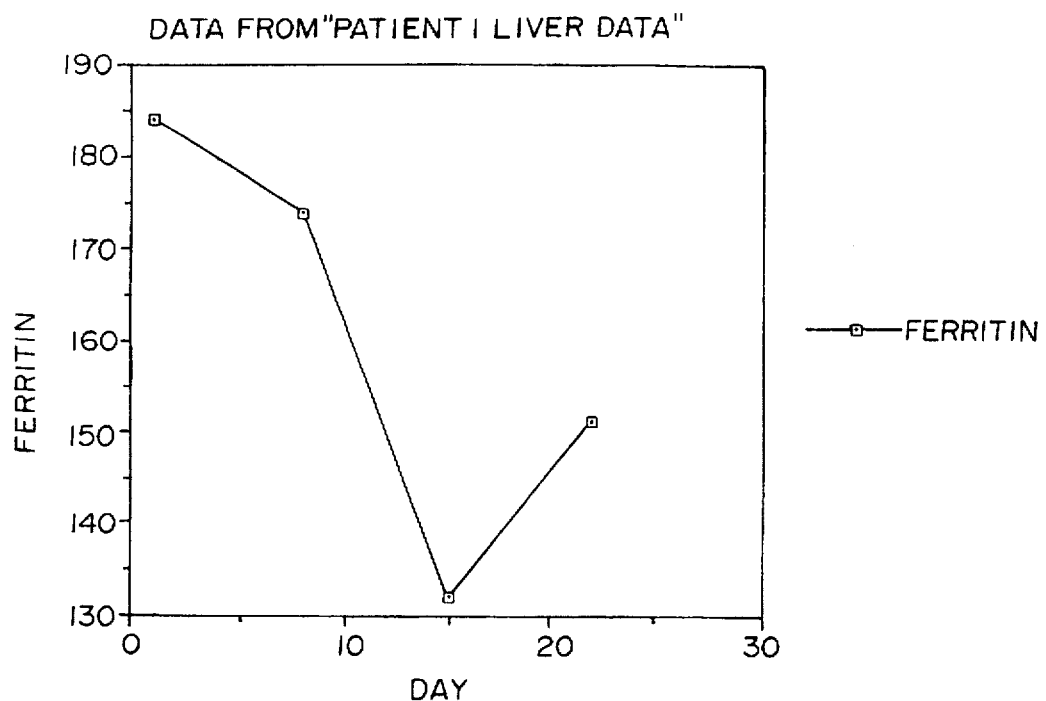

Patient 1 Demonstrating Reduction in Plasma Levels of Liver Enzymes During Course of Biaxin Treatment Patient 1, a 50 year old white male was diagnosed as having nonalcoholic steatohepatitis and began Biaxin™ treatment every other day for 22 days. Of interest, this patient has been followed since mid-1986 and since 1992 presented with increased ALT levels and rising AST levels. This patient's data are presented in Table 2 and the data are graphed in FIGS. 1A to 1C.

This patient demonstrated a −64.4% change in AST levels, a −66.2% change in ALT levels, a 11.7% change in GGT levels, and a −17.9% change in ferritin levels.

Example 6

Figure 2:
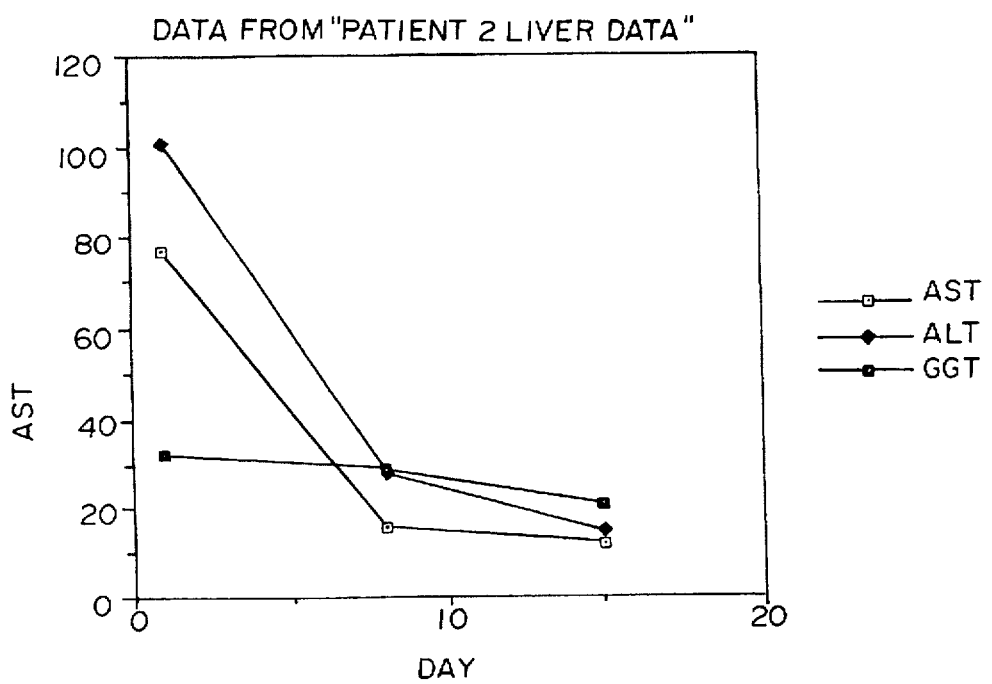
FIG. 2 Presents liver enzyme levels for Patient #2.

Patient 2 Demonstrating Reduction in Plasma Levels of Liver Enzymes During Course of Biaxin Treatment Patient 2, a 36 year old white female was diagnosed as having nonalcoholic steatohepatitis and began Biaxin™ treatment every other day for 15 days. This patient's data are presented in Table 2 and the data are graphed in FIG. 2.

This patient demonstrated a −84.4% change in AST levels, a −85.1% change in ALT levels, and a −34.4% change in GGT levels.

Example 7

Figure 3A:
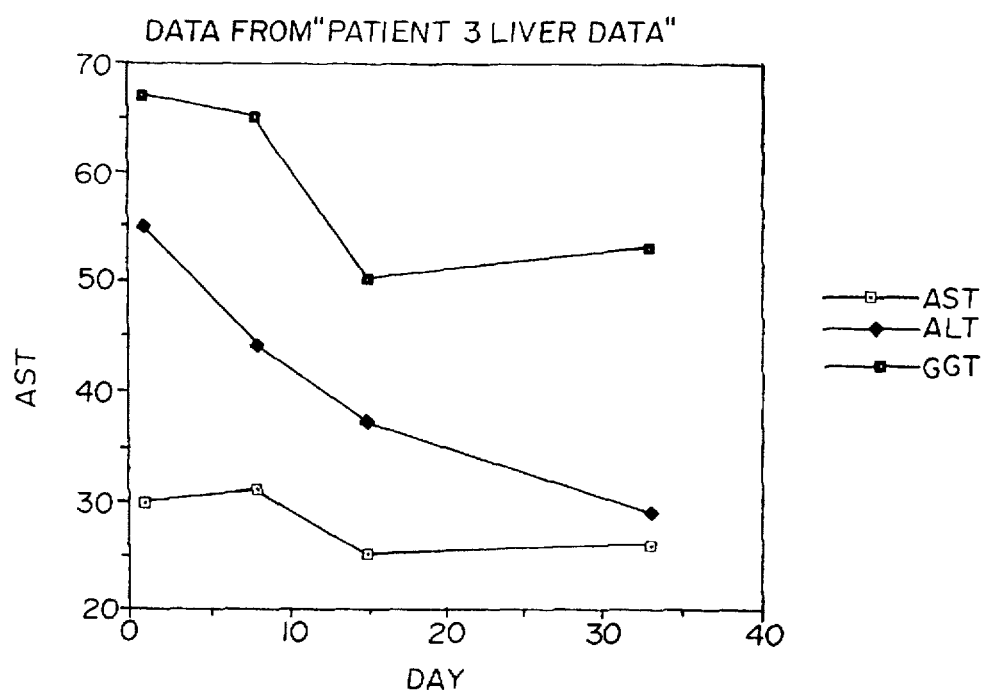
FIG. 3 Panels A and B detail liver enzyme levels for Patient #3.
Figure 3B:
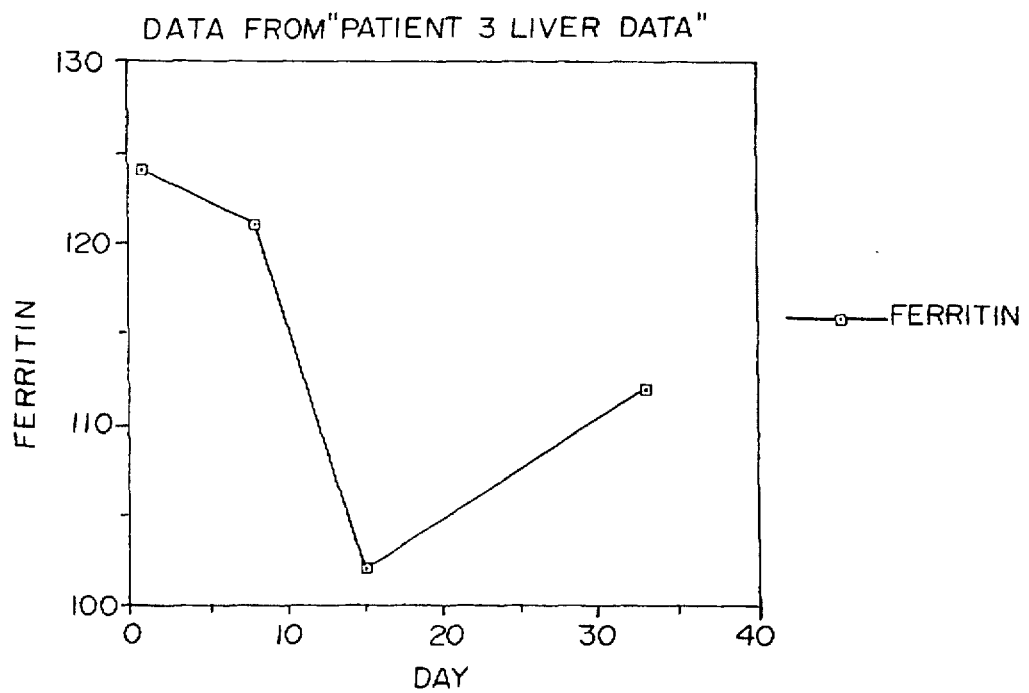
Figure 4A:
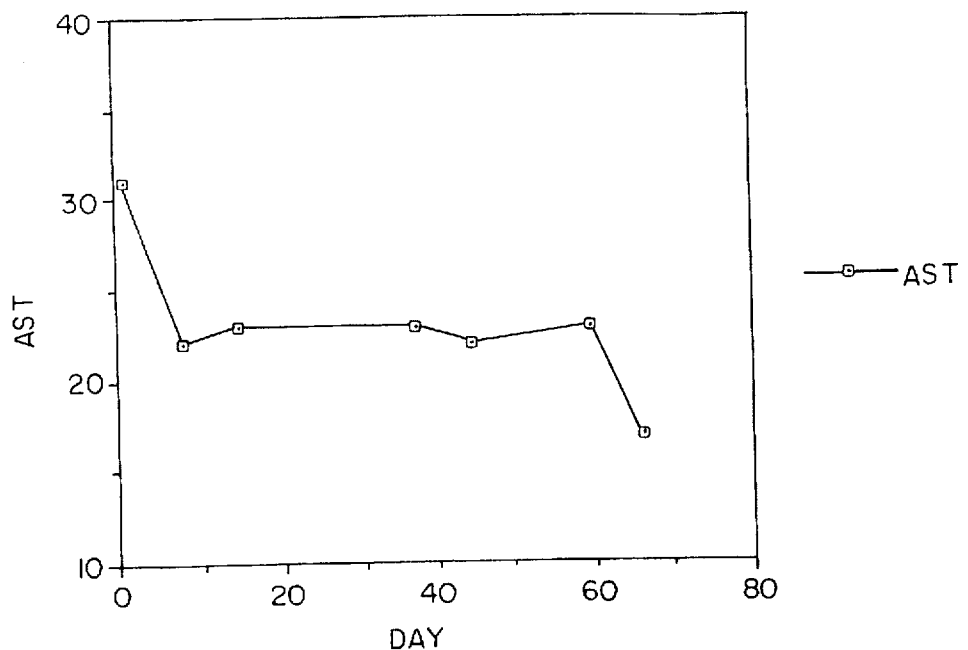
FIG. 4 Panels A, B, C, and D detail liver enzyme levels for Patient #4.
Figure 4B:
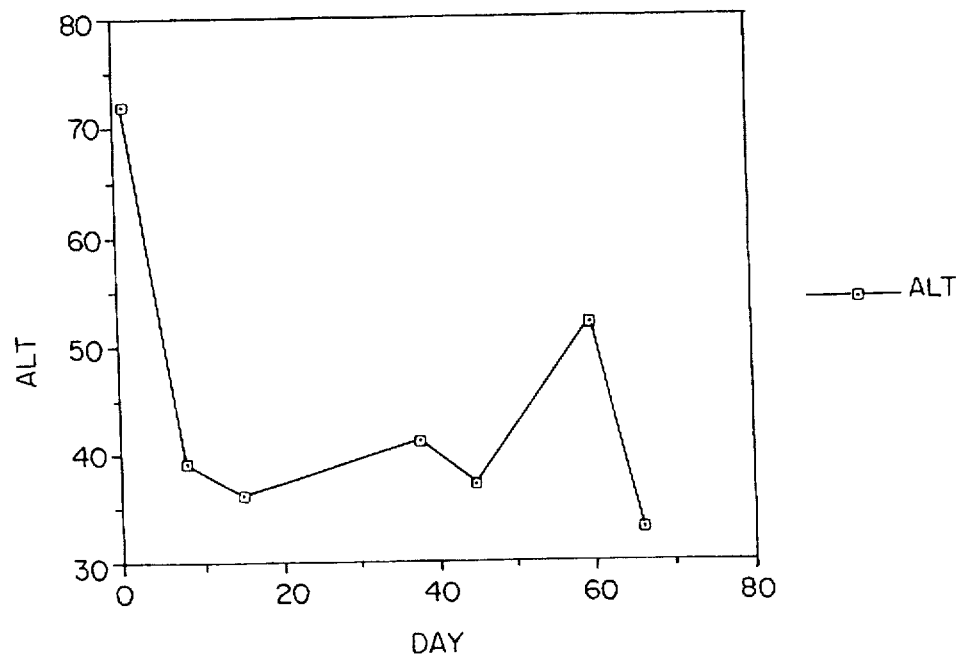
Figure 4C:
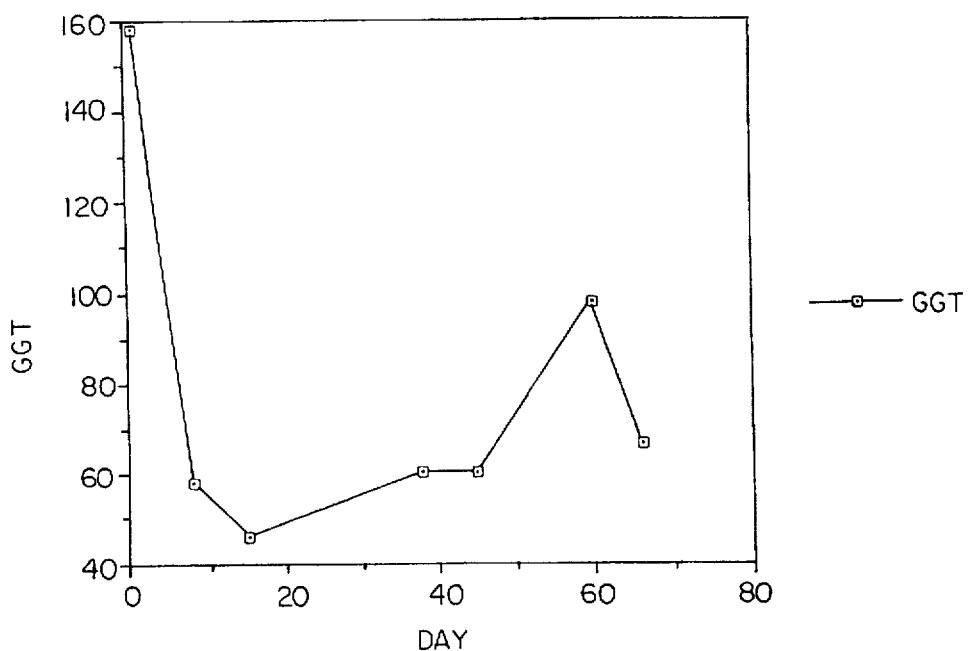
Figure 4D:
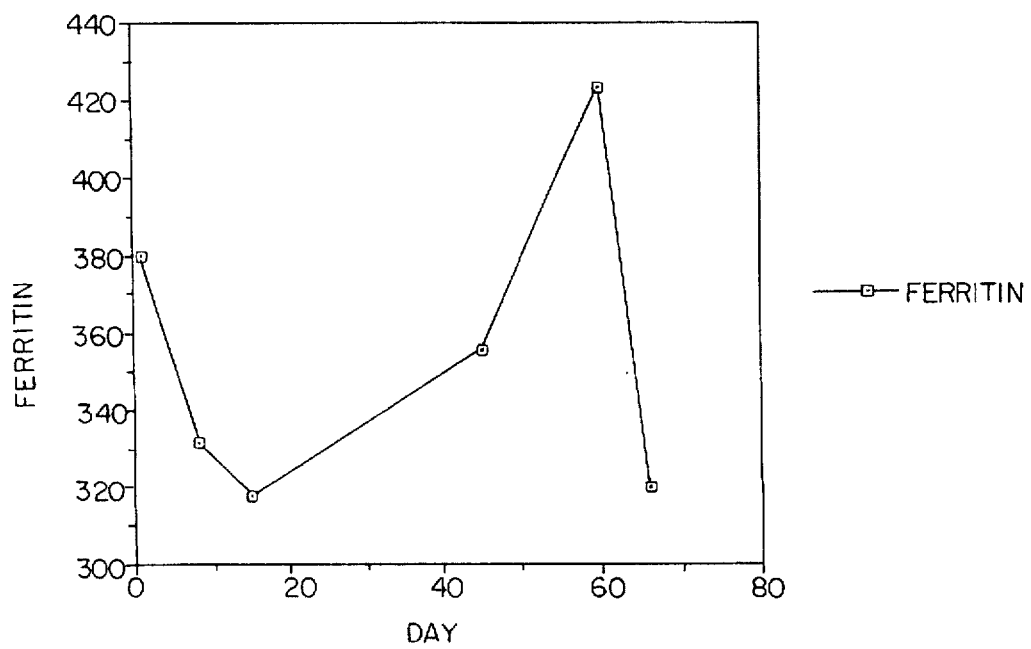

Patient 3 Demonstrating Reduction in Plasma Levels of Liver Enzymes During Course of Biaxin Treatment Patient 3, a 38 year old white female was diagnosed as having nonalcoholic steatohepatitis and began Biaxin™ treatment every other day for 33 days. This patient's data are presented in Table 2 and the data are graphed in FIGS. 3A to 3B.

This patient demonstrated a −13.3% change in AST levels, a −47.3% change in ALT levels, a −20.9% change in GGT levels, and a −9.7 change in ferritin levels.

Example 8

Therapeutic Administration of Erythromycin or Erythromycin Derived Compounds for Treating Alcoholic Hepatitis An alternative aspect of this invention is novel method of treating liver disorders or liver diseases including alcoholic hepatitis. Yet another preferred aspect of the present invention is a method of treating alcoholic hepatitis which includes the administration of an effective amount of an erythromycin compound. Many different erythromycin compounds or erythromycin derived compounds are known to those skilled in this art but the inventors prefer to use erythromycin, clarithromycin, azithromycin, or troleandomycin. The routes of administration can include oral, intramuscular, subcutaneous, transdermal, intravenous or other common routes of administering a drug to a patient. Alternate routes for patients diagnosed with alcoholic hepatitis are extremely important as oral administration would not be effective due to the patient's clinical symptoms.

A patient in need of treatment for alcoholic hepatitis may be identified by measuring plasma levels of liver enzymes (e.g., GGT, AST, ALT), or by other standard diagnostic techniques (e.g., liver biopsy, patient history of malnutrition or alcoholism, etc.). Informed patient consent is obtained and treatment is initiated. A complete medical history is obtained with emphasis on potential adverse reactions to or contraindications for the use of erythromycin compounds. Blood is drawn from the patient and plasma levels of different liver enzymes are determined. The desired reduction of plasma levels of liver enzymes is then determined based upon a comparison of the patient's present plasma enzyme levels with normative values and the physician's professional judgment. An effective dose for treating alcoholic hepatitis, the interval between doses, and the duration of treatment are then determined. The patient is followed at appropriate intervals during treatment and measurements of plasma levels of liver enzymes, patient histories, and dose modification, if necessary, are performed.

Three patients with diagnosed alcoholic hepatitis were treated with clarithromycin (10 mg/pound of body weight at 48 hour intervals for the days indicated). Five milliliters of blood were drawn from each patient on the indicated days and plasma levels of AST, ALT, and GGT were determined for each patient. The results of such a treatment regime are shown in Table 3.

General conclusions after fifteen (15) days of Biaxin™ treatment for these initial three (3) patients demonstrated that:
1. Plasma AST levels decreased by greater than or equal to 10% in 3 out of 3 patients (100%).
2. Plasma ALT levels decreased by greater than or equal to 10% in 3 out of 3 patients (100%).
3. Plasma GGT levels decreased by greater than or equal to 10% in 3 out of 3 patients (100%).
4. Plasma ferritin levels decreased by greater than or equal to 10% in 2 out of 3 patients (67%).

Example 9

Patient 4 Demonstrating Reduction in Plasma Levels of Liver Enzymes During Course of Biaxin Treatment Patient 4, a 39 year old white male was diagnosed as having alcoholic hepatitis and began Biaxin™ treatment every other day for 66 days. Note that this patient was off Biaxin on days 53–60 and resumed Biaxin treatment on day 61. This patient's data are presented in Table 3 and the data are graphed in FIGS. 4A to 4D.

This patient demonstrated a −45.2% change in AST levels, a −54.2% change in ALT levels, a −57.6% change in GGT levels, and a −16.4% change in ferritin levels.

Example 10

Figure 5A:
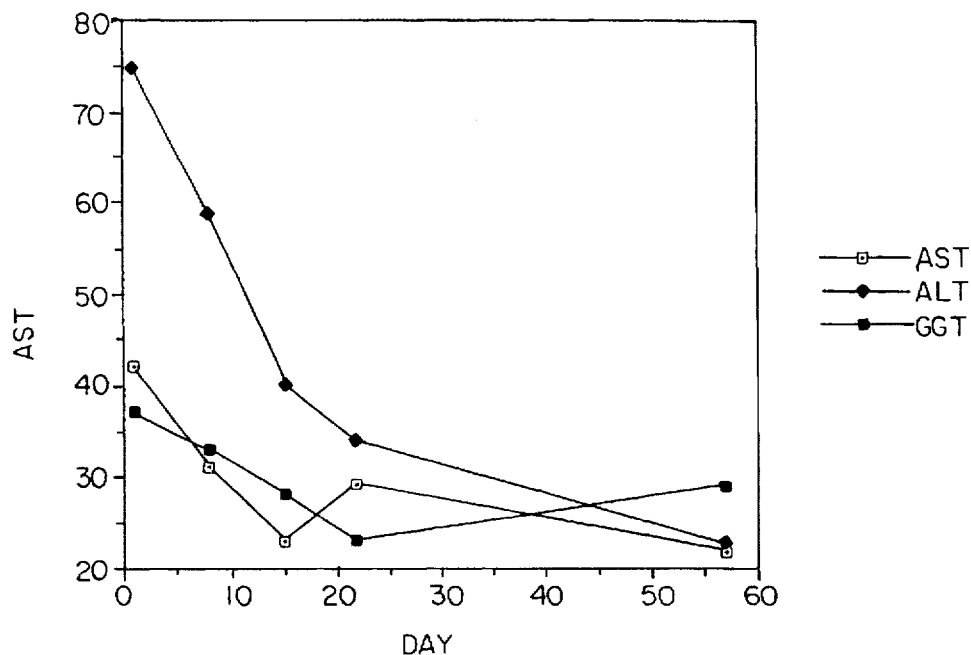
FIG. 5 Panels A and B detail liver enzyme levels for Patient #5.
Figure 5B:
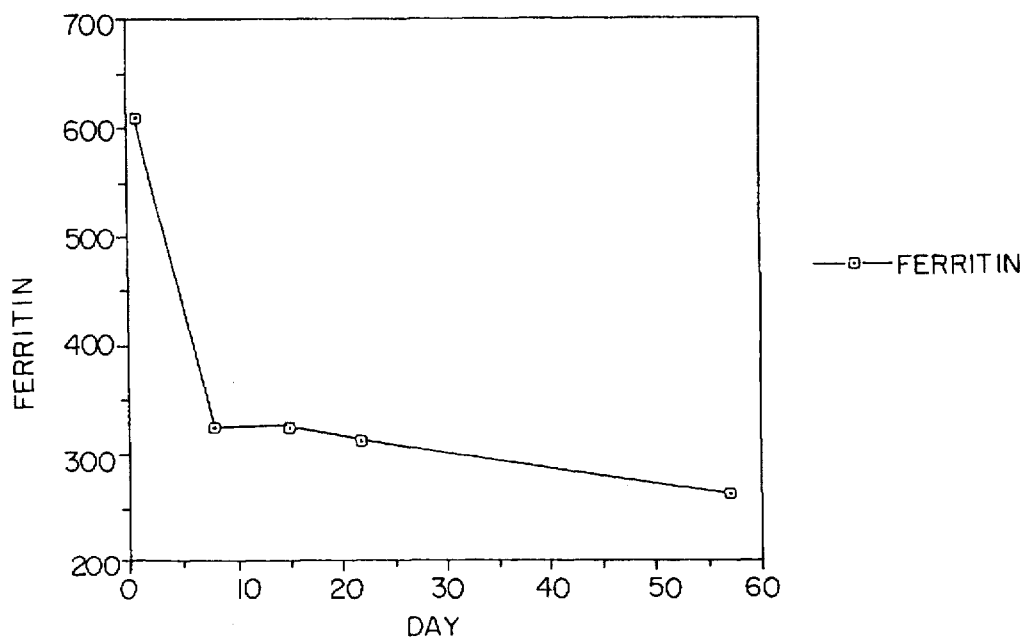

Patient 5 Demonstrating Reduction in Plasma Levels of Liver Enzymes During Course of Biaxin Treatment Patient 5, a 51 year old white male was diagnosed as having alcoholic hepatitis and began Biaxin™ treatment every other day for 57 days. This patient was off of Biaxin from days 23–57. This patient's data are presented in Table 3 and the data are graphed in FIGS. 5A to 5B.

This patient demonstrated a −47.6% change in AST levels, a −69.3% change in ALT levels, a −21.6% change in GGT levels, and a −56.3 change in ferritin levels.

Example 11

Figure 6A:
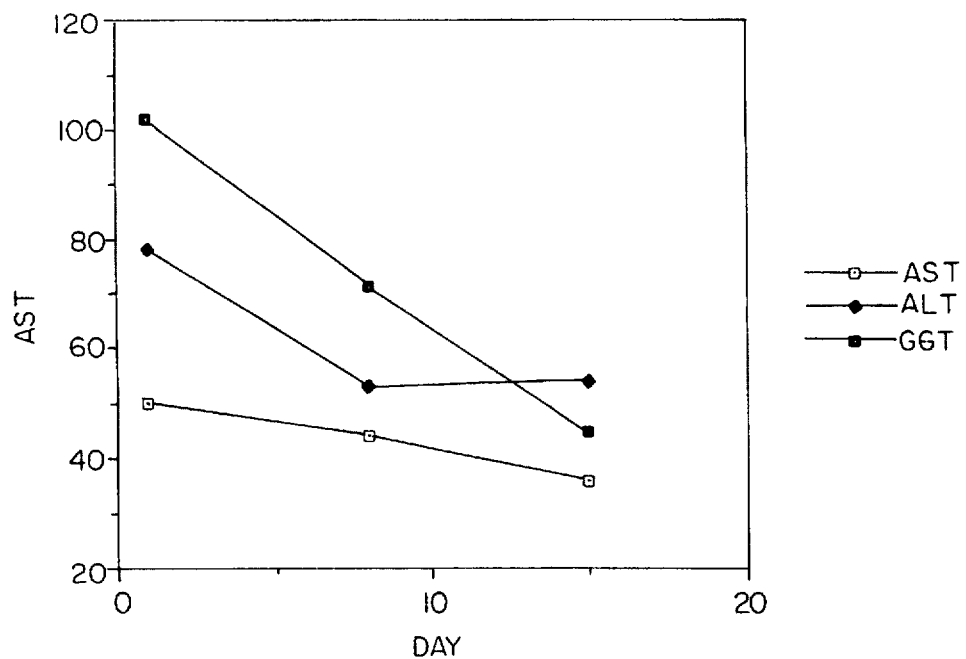
FIG. 6 Panels A and B detail liver enzyme levels for Patient #6.
Figure 6B:
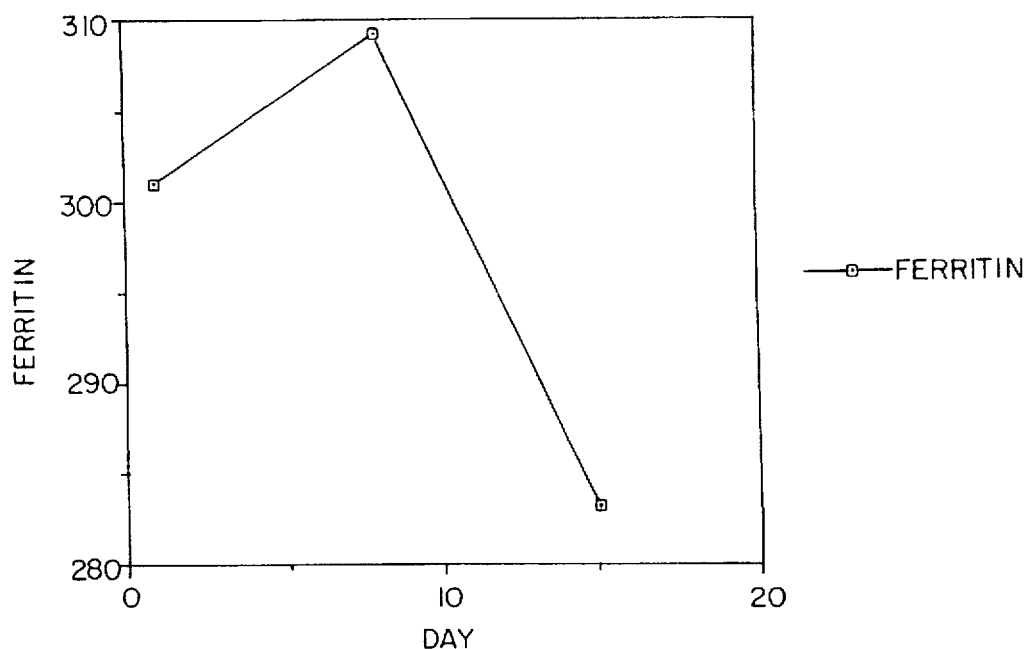

Patient 6 Demonstrating Reduction in Plasma Levels of Livers Enzymes During Course of Biaxin Treatment Patient 6, a 40 year old white male was diagnosed as having alcoholic hepatitis and began Biaxin™ treatment every other day for 15 days. This patient's data are presented in Table 3 and the data are graphed in FIGS. 6A to 6B.

This patient demonstrated a −28.0% change in AST levels, a −30.8% change in ALT levels, a −55.9% change in GGT levels, and a −6.0 change in ferritin levels.

Example 12

Therapeutic Administration of Erythromycin or Erythromycin Derived Compounds for Treating Reye's Syndrome An alternative aspect of this invention is novel method of treating liver disorders or liver diseases including Reye's Syndrome. Yet another preferred aspect of the present invention is a method of treating Reye's Syndrome which includes the administration of an effective amount of an erythromycin compound. Many different erythromycin compounds or erythromycin derived compounds are known to those skilled in this art but the inventor prefers to use erythromycin, clarithromycin, azithromycin, or troleandomycin. The routes of administration can include oral, intramuscular, subcutaneous, transdermal, intravenous or other common routes of administering a drug to a patient. Alternate routes for patients diagnosed with Reye's Syndrome are extremely important as oral administration would not be effective due to the patient's clinical symptoms.

A patient in need of treatment for Reye's Syndrome will be identified by measuring plasma levels of liver enzymes (e.g., GGT, AST, ALT, ammonia, and prothrombin time), or by other standard diagnostic techniques (e.g., liver biopsy, etc.) and monitored on a daily basis. Informed consent will be obtained from the parent and treatment will then be initiated. A complete medical history will be obtained with emphasis on potential adverse reactions to or contraindications for the use of erythromycin compounds. Blood will be drawn from the patient and plasma levels of different liver enzymes will be determined. The desired reduction of plasma levels of liver enzymes will be determined based upon a comparison of the patient's current plasma enzyme levels with normative values and the physician's professional judgment. An effective dose for treating Reye's Syndrome, the interval between doses, and the duration of treatment will then determined. The patient will be followed at appropriate intervals during treatment and measurements of plasma levels of liver enzymes, patient histories, and dose modification, if necessary, will be performed. The improvement or progress of each patient will be monitored on at least a daily basis.

The patients with diagnosed Reye's Syndrome will be treated with clarithromycin (1 mg–100 mg/pound of body weight at 24 or 48 hour intervals; dose and duration will be determined on a case-by-case basis). Five milliliters of blood will be drawn be from each patient and plasma levels of AST, ALT, GGT, ammonia, and prothrombin time will be determined for each patient.

References

The following references may facilitate understanding or practice of certain aspects of the present invention. Inclusion of a reference in this list is not intended to and does not constitute an admission that the reference represents prior art with respect to the present invention.

Achord, J. L., *Review of Alcoholic Hepatitis, and Its Treatment*, The American Journal of Gastroenterology, 88(11):1822–1828, 1993.

Bacon et al, *Nonalcoholic Steatohepatitis: An Expanded Clinical Entity*, Gastroenterology, 107:1103–1109, 1994.

Bryskier, A., Agouridas, C., and Chantot, J. F., *Structure and Activity in* THE NEW MACROLIDES, AZALIDES, AND STREPTOGRAMINS: PHARMACOLOGY AND CLINICAL APPLICATIONS, 3,3–11, Neu, H. C., Young, L. S., and Zinner, S. H., eds., 1993.

Cohen et al, *The SGOT/SGPT Ratio: An Indicator of Alcoholic Liver Disease*, Dig. Dis. Sci., 24:835–838 1979.

Goldberg, et al, *VA Cooperative Study on Alcoholic Hepatitis IV*, American Journal of Gastroenterology, 81:1029–1034, 1986.

Gregory, P. G. *Cirrhosis of the Liver* in Scientific American Medicine for Gastroenterology, pp. 1–18, 1995.

Isselbacher, K. J. and D. K. Podosky, *Infiltrative and Metabolic Diseased affecting the Liver* in Harrison's Principles of Internal Medicine eds Brawnwald, E. et al pp. 1353–54, 1988.

Ludwig et al., *Nonalcoholic Steatohepatitis. Mayo Clinic Experiences With A Hitherto Unnamed Disease,* Mayo Clinic Proceedings, 55:434–438, 1980.

*Metropolitan Height and Weight Tables.* New York: Metropolitan Life Insurance Company, 1983.

Omura, S., *Macrolide Antibiotics—Chemistry, Biology and Practice* 1984.

Physicians' Desk Reference®, 405–407, 1789–91, 421–423, 425–427, 449, 651, 935, 937, 1841, and 2102, 1994.

Physicians' Desk Reference, 2419, 1995.

Reye, et al, *Encephalopathy and fatty degeneration of the viscera.* Lancet, 2:749, 1963.

Schubert et al, *Encephalopathy and Fatty Liver (Reye's Syndrome),* IN: Popper, H. and Schaffner, F. (Eds.): Progress in Liver Diseases. Chap. 28, 4th Edition, New York, Grune and Stratton, Inc., 1972, pp. 489–510.

U.S. Pat. No. 4,331,803, Issued to Watanabe.

U.S. Pat. No. 4,482,540, Issued to Gordon et al on Nov. 13, 1984.

Alternative aspects of the present invention are described within the following claims. In addition, modes alternative to oral administration may be used (e.g., intravenous, intramuscular, intraperitoneal, topical, or the like). Moreover, macrolide antibiotic compounds may be administered on a continuous or an intermittent basis.

The foregoing description has been directed to particular embodiments of the invention in accordance with the Patent Statutes for the purposes of illustration and explanation. It will be apparent, however, to those skilled in this art that many modifications, changes and variations in the claimed invention will be possible without departing from the scope and spirit of the claimed invention. It is intended that the following claims be interpreted to embrace all such modifications and changes.

TABLE 2

EFFECT OF CLARITHROMYCIN ON PLASMA LEVELS OF LIVER ENZYMES IN PATIENTS WITH NONALCOHOLIC STEATOHEPATITIS

|   | DAY | AST | % CHANGE | ALT | % CHANGE | GGT | % CHANGE | FERRITIN | % CHANGE |
|---|---|---|---|---|---|---|---|---|---|
| | | | | PATIENT 4 LIVER DATA | | | | | |
| 1 | 1.000 | 90.000 | | 151.000 | | 240.000 | | 184.000 | |
| 2 | 8.000 | 70.000 | −22.200 | 158.000 | 4.600 | 368.000 | 53.300 | 174.000 | −5.400 |
| 3 | 15.000 | 38.000 | −57.800 | 98.000 | −35.100 | 343.000 | 42.900 | 132.000 | −28.300 |
| 4 | 22.000 | 32.000 | −64.400 | 51.000 | −66.200 | 268.000 | 11.700 | 151.000 | −17.900 |
| | | | | PATIENT 19 LIVER DATA | | | | | |
| 1 | 1.000 | 77.000 | | 101.000 | | 32.000 | | | |
| 2 | 8.000 | 16.000 | −79.200 | 28.000 | −72.300 | 29.000 | −9.400 | | |
| 3 | 15.000 | 12.000 | −84.400 | 15.000 | −85.100 | 21.000 | −34.400 | | |
| | | | | PATIENT 5 LIVER DATA | | | | | |
| 1 | 1.000 | 30.000 | | 55.000 | | 67.000 | | 124.000 | |
| 2 | 8.000 | 31.000 | 3.300 | 44.000 | −20 | 65.000 | −3.000 | 121.000 | −2.400 |
| 3 | 15.000 | 25.000 | −16.700 | 37.000 | −32.7 | 50.000 | −25.400 | 102.000 | −17.700 |
| 4 | 33.000 | 26.000 | −13.300 | 29.000 | −47.3 | 53.000 | −20.900 | 112.000 | −9.700 |

TABLE 3

EFFECT OF CLARITHROMYCIN ON PLASMA LEVELS OF LIVER ENZYMES IN PATIENTS WITH ALCOHOLIC HEPATITIS

|   | DAY | AST | % CHANGE | ALT | % CHANGE | GGT | % CHANGE | FERRITIN | % CHANGE |
|---|---|---|---|---|---|---|---|---|---|
| | | | | PT. 9 LIVER DATA | | | | | |
| 1 | 1.000 | 31.000 | | 72.000 | | 158.000 | | 380.000 | |
| 2 | 8.000 | 22.000 | −29.000 | 39.000 | −45.800 | 58.000 | −63.300 | 332.000 | |
| 3 | 15.000 | 23.000 | −25.800 | 36.000 | −50.000 | 46.000 | −70.900 | 318.000 | |
| 4 | 38.000 | 23.000 | −25.800 | 41.000 | −43.100 | 60.000 | −62.000 | | |
| 5 | 45.000 | 22.000 | −29.000 | 37.000 | −48.600 | 60.000 | −62.000 | 356.000 | |
| 6 | 60.000 | 23.000 | −25.800 | 52.000 | −27.800 | 98.000 | −38.000 | 423.000 | |
| 7 | 66.000 | 17.000 | −45.200 | 33.000 | −54.200 | 67.000 | −57.600 | 320.000 | |
| | | | | PATIENT 13 LIVER DATA | | | | | |
| 1 | 1.000 | 42.000 | | 75.000 | | 37.000 | | 607.000 | |
| 2 | 8.000 | 31.000 | −26.200 | 59.000 | −21.300 | 33.000 | −10.800 | 324.000 | −46.600 |
| 3 | 15.000 | 23.000 | −45.200 | 40.000 | −46.700 | 28.000 | −24.300 | 324.000 | −46.600 |
| 4 | 22.000 | 29.000 | −31.000 | 34.000 | −54.700 | 23.000 | −37.800 | 311.000 | −48.800 |
| 5 | | | | | | | | | |
| 6 | 57.000 | 22.000 | −47.600 | 23.000 | 69.300 | 29.000 | −21.600 | 265.000 | −56.300 |
| | | | | PATIENT 14 LIVER DATA | | | | | |
| 1 | 1.000 | 50.000 | | 78.000 | | 102.000 | | 301.000 | |

TABLE 3-continued

EFFECT OF CLARITHROMYCIN ON PLASMA LEVELS OF LIVER ENZYMES IN PATIENTS WITH ALCOHOLIC HEPATITIS

| DAY | AST | % CHANGE | ALT | % CHANGE | GGT | % CHANGE | FERRITIN | % CHANGE |
|---|---|---|---|---|---|---|---|---|
| 2 | 8.000 | 44.000 | −12.000 | 53.000 | −32.100 | 71.000 | −30.400 | 309.000 | 2.700 |
| 3 | 15.000 | 36.000 | −28.000 | 54.000 | 30.800 | 45.000 | −55.900 | 283.000 | −6.000 |

What is claimed is:

1. A method of treating a human having a liver disorder characterized by supranormal plasma activity of a liver aminotransferase comprising administering to the human an effective dose for treating a liver disorder of an erythromycin compound.

2. The method of claim 1, wherein the erythromycin compound is selected from the group consisting of clarithromycin, troleandomycin, erythromycin, and azithromycin.

3. The method of claim 1, wherein the dose is administered orally and ranges from 100 mg/day to 6,000 mg/day.

4. The method of claim 1, wherein the dose ranges from about 1 mg/kg of body weight/day to about 100 mg/kg of body weight/day.

5. A method of reducing the supranormal plasma activity of a liver enzyme in a human comprising administering to the human an effective dose for reducing the plasma activity of a liver enzyme of an erythromycin compound.

6. The method of claim 5, wherein the liver enzyme is selected from the group consisting of an aminotransferase and a transpeptidase.

7. The method of claim 6, wherein the aminotransferase is selected from the group consisting of aspartate aminotransferase and alanine aminotransferase.

8. The method of claim 6, wherein the transpeptidase comprises γ-glutamyl transpeptidase.

9. The method of claim 5, wherein the erythromycin compound is selected from the group consisting of clarithromycin, troleandomycin, erythromycin, and azithromycin.

10. The method of claim 5, wherein the dose is administered orally and ranges from 100 mg/day to 6,000 mg/day.

11. The method of claim 5, wherein the dose ranges from about 1 mg/kg of body weight/day to about 100 mg/kg of body weight/day.

12. The method of claim 1, further comprising reducing the plasma activity of the liver aminotransferase.

13. The method of claim 1, wherein the aminotransferase is selected from the group consisting of aspartate aminotransferase and alanine aminotransferase.

14. The method of claim 1, wherein the liver disorder is further characterized by a supranormal plasma activity of a liver transpeptidase, a supranormal serum iron concentration, a supranormal hepatic iron concentration, or any combination thereof.

15. The method of claim 14, wherein the transpeptidase comprises γ-glutamyl transpeptidase.

16. The method of claim 14, further comprising reducing the plasma activity of the liver transpeptidase.

17. The method of claim 14, further comprising reducing the serum iron concentration.

18. The method of claim 14, further comprising reducing the hepatic iron concentration.

19. The method of claim 1, wherein the dose is about 11 mg/kg of body weight/day.

20. The method of claim 1, wherein the dose is about 22 mg/kg of body weight/day.

21. The method of claim 1, wherein the liver disorder is selected from the group consisting of nonalcoholic steatohepatitis, alcoholic hepatitis, and Reye's syndrome.

22. A method of treating a human having a liver disorder characterized by a supranormal plasma activity of a liver aminotransferase, comprising:

administering to the human dose of an erythromycin compound ranging from about 1 mg/kg of body weight to about 100 mg/kg of body weight; and wherein the liver disorder is selected from the group consisting of nonalcoholic steatohepatitis, alcoholic hepatitis, and Reye's Syndrome.

23. A method of treating a human having a liver disorder characterized by a supranormal plasma activity of a liver aminotransferase, comprising:

administering to the human a dose of clarithromycin ranging from about 1 mg/kg of body weight/day to about 100 mg/kg of body weight/day;

reducing the plasma activity of the liver aminotransferase; and wherein the liver disorder is selected from the group consisting of nonalcoholic steatohepatitis, alcoholic hepatitis, and Reye's Syndrome.

24. A method of treating a human having a liver disorder characterized by supranormal lipid accumulation in the liver comprising administering to the human an effective dose for treating a liver disorder of an erythromycin compound.

25. The method of claim 24, wherein the erythromycin compound is selected from the group consisting of clarithromycin, troleandomycin, erythromycin, and azithromycin.

26. The method of claim 24, wherein the dose is administered orally and ranges from 100 mg/day to 6,000 mg/day.

27. The method of claim 24, wherein the dose ranges from about 1 mg/kg of body weight/day to about 100 mg/kg of body weight/day.

28. The method of claim 24, wherein the liver disorder is further characterized by a supranormal plasma activity of a liver aminotransferase.

29. The method of claim 28, further comprising reducing the plasma activity of the liver aminotransferase.

30. The method of claim 28, wherein the aminotransferase is selected from the group consisting of aspartate aminotransferase and alanine aminotransferase.

31. The method of claim 24, wherein the liver disorder is further characterized by a supranormal plasma activity of a liver transpeptidase, a supranormal serum iron concentration, a supranormal hepatic iron concentration or any combination thereof.

32. The method of claim 31, wherein the transpeptidase comprises γ-glutamyl transpeptidase.

33. The method of claim 31, further comprising reducing the plasma activity of the liver transpeptidase.

34. The method of claim 31, further comprising reducing the serum iron concentration.

35. The method of claim 34, further comprising reducing the hepatic iron concentration.

36. The method of claim 24, wherein the dose is about 11 mg/kg of body weight/day.

37. The method of claim 24, wherein the dose is about 22 mg/kg of body weight/day.

38. The method of claim 24, wherein the liver disorder is selected from the group consisting of nonalcoholic steatohepatitis, alcoholic hepatitis, and Reye's syndrome.

39. The method of claim 24, further comprising reducing lipid accumulation in the liver.

40. A method of treating a human having a liver disorder characterized by supranormal lipid accumulation in the liver, comprising:
    administering to the human a dose of an erythromycin compound ranging from about 1 mg/kg of body weight/day to about 100 mg/kg of body weight/day; and
    wherein the disorder is selected from the group consisting of nonalcoholic steatohepatitis, alcoholic hepatitis, and Reye's Syndrome.

41. A method of treating a human having a liver disorder characterized by supranormal lipid accumulation in the liver, comprising:
    administering to the human a dose of clarithromycin ranging from about 1 mg/kg of body weight/day to about 100 mg/kg of body weight/day;
    reducing the lipid accumulation in the liver; and
    wherein the disorder is selected from the group consisting of nonalcoholic steatohepatitis, alcoholic hepatitis, and Reye's Syndrome.

42. The method of claim 5, further comprising reducing a supranormal serum iron concentration of the human.

43. The method of claim 5, further comprising reducing a supranormal hepatic iron concentration of the human.

44. The method of claim 5, further comprising reducing lipid accumulation in the liver.

45. The method of claim 5, wherein the dose is about 11 mg/kg of body weight/day.

46. The method of claim 5, wherein the dose is about 22 mg/kg of body weight/day.

47. The method of claim 5, wherein the human has a liver disorder characterized by supranormal lipid accumulation in the liver.

48. The method of claim 5, wherein the human has a liver disorder selected from the group consisting of nonalcoholic steatohepatitis, alcoholic hepatitis, or Reye's Syndrome.

49. A method of reducing the supranormal plasma activity of a liver aminotransferase or transpeptidase in a human comprising administering to the human a dose of an erythromycin compound ranging from about 1 mg/kg of body weight/day to about 100 mg/kg of body weight/day.

50. A method of reducing the supranormal plasma activity of a liver enzyme selected from the group consisting of aspartate aminotransferase, alanine aminotransferase, and γ-glutamyl transpeptidase in a human comprising administering to the human a dose of clarithromycin ranging from about 1 mg/ky of body weight/day to about 100 mg/kg of body weight/day.

* * * * *